United States Patent [19]

Okada et al.

[11] Patent Number: 4,810,083
[45] Date of Patent: Mar. 7, 1989

[54] BINOCULAR INDIRECT OPHTHALMOSCOPE

[75] Inventors: Kohichi Okada; Kazutoshi Takagi, both of Tokyo, Japan

[73] Assignees: Kabushiki Kaisha Naitsu; Tokyo Kogaku Kikai Kabushiki Kaisha, both of Tokyo, Japan

[21] Appl. No.: 188,380

[22] Filed: Apr. 29, 1988

[30] Foreign Application Priority Data

Apr. 30, 1987 [JP] Japan ............................. 62-66279[U]

[51] Int. Cl.⁴ ................................................ A61B 3/10
[52] U.S. Cl. ..................................... 351/205; 351/211; 351/245
[58] Field of Search ................. 351/205, 211, 214, 245

[56] References Cited

U.S. PATENT DOCUMENTS 4,219,257 8/1980 Slappey et al. ..................... 351/205

Primary Examiner—Rodney B. Bovernick
Attorney, Agent, or Firm—Finnegan, Henderson, Farabow, Garrett & Dunner

[57] ABSTRACT

The invention provides a binocular indirect ophthalmoscope in which light reflected from an eye under test is split and guided to left and right oculars (7, 8). Left and right mirrors (10, 11) for directing the split light to the left and right oculars being laterally movable about the optical axes (01, 02) of the oculars and toward and away from each other. The mirrors are arranged to follow the mutual approaching and receding of the oculars but the oculars will not follow the mutual approaching and receding of the mirrors, whereby the distance between these mirrors can be adjusted separately from the distance between the optical axes of the oculars.

Such arrangement allows the operator to shift the light beams for observation (OFL, OFR) to appropriate positions where they are not interrupted by the iris, and thus allows sufficient and widely ranging stereoscopic observation, irrespective of the size of the pupil diameter of the eye under test or OF the direction of observation. Further, the distance between the oculars can easily and rapidly be adjusted for adaptation to different operators having different eye-to-eye distances.

7 Claims, 5 Drawing Sheets

FIG. 7 PRIOR ART
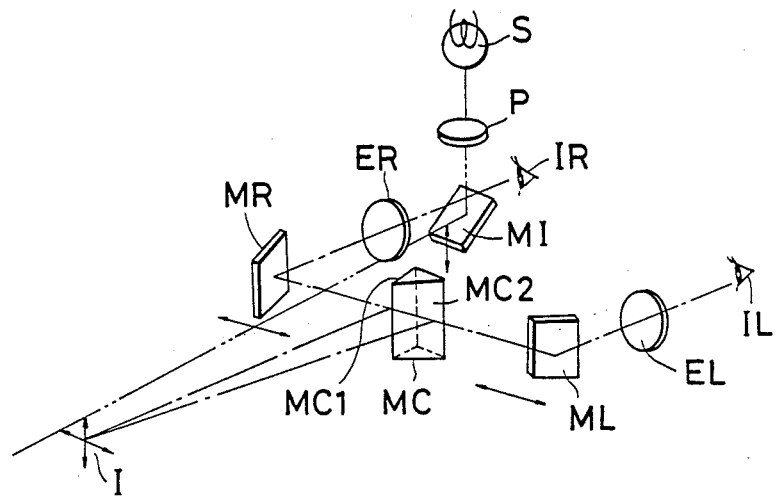
FIG. 8A PRIOR ART
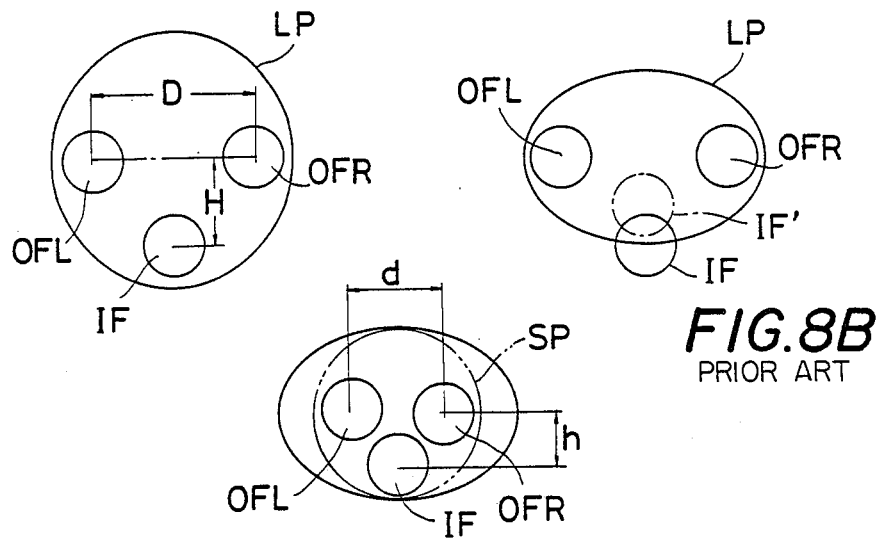
FIG. 8B PRIOR ART
FIG. 8C PRIOR ART

BINOCULAR INDIRECT OPHTHALMOSCOPE

BACKGROUND OF THE INVENTION

1. Field of the Invention

The present invention relates in general to a binocular indirect ophthalmoscope for stereoscopically observing an eye fundus, for example, and in particular to an apparatus of such type having a movable illuminating-light deflector and movable observation-light deflectors.

2. Description of the Prior Art

FIG. 7 shows a prior art binocular indirect ophthalmoscope of the above-described type. In this prior art apparatus, light from an illuminating light source S is projected to the fundus of an eye under test (not shown) through a projection lens P and through an illuminating-light deflector in the form of a mirror MI. In this binocular indirect ophthalmoscope, an aerial image I of the eye fundus is formed by an aspherical lens (not shown), and light from the aerial image I is split into left and right light beams by two reflecting surfaces MC1, MC2 of a center mirror MC. One of these two light beams passes via an observation-light deflector in the form of a mirror MR and via an ocular ER to the right eye of the operator, while the other light beam passes via another observation-light deflector in the form of another mirror ML and via another ocular EL to the left eye of the operator. This allows the operator to stereoscopically observe the fundus of the eye under test.

When the peripheral regions of an eye fundus should be observed by means of such a prior art indirect ophthalmoscope, it must be observed obliquely from above or from below even if the eye under test has a relatively large pupil LP (see FIG. 8A). However, there is a difficulty in that the effective illuminating light beam can be partially interrupted by the iris of an eye having a relatively large pupil LP when its fundus peripheral regions are observed obliquely from above or from below, because the relatively large pupil LP then appears elliptic, laterally elongated as shown in FIG. 8B.

To obviate such difficulty, said mirror MI may be interlocked with the other mirrors MR, ML in such a manner that the distance D between the effective observation light beams OFR, OFL on the pupil plane and the distance H to the effective illuminating light beam IF can be changed simultaneously, whereby eyes with larger pupils LP shown in FIG. 8A, as well as eyes with smaller pupils SP shown in a two-dot long and two short dashes line in FIG. 8C can be observed.

However, in such an arrangement, when the mirror MI is moved to reduce the distance to the effective illuminating light beam from H to h (H is larger than h), the other mirrors MR, ML will simultaneously move toward each other, with the result that the distance between the effective observation light beams OFR, OFL is reduced from D to d (D is larger than d), deteriorating the stereoscopic sensation as provided by such apparatus.

Further, the distance between the optical axes of the right combination of the right mirror MR and right ocular ER and of the left combination of the left mirror ML and left ocular EL must be adjustable for adaptation to the pupil-to-pupil distance IR-IL of the operator's eyes. However, the mirrors MR, ML must be movable independently from the oculars ER, EL in order that smaller-pupilled eyes can be observed. Such a requirement is not satisfied by any prior art.

SUMMARY OF THE INVENTION

An object of the present invention is therefore to obviate the difficulties found in such prior art binocular indirect ophthalmoscope. The principal object of the invention is to provide an improved binocular indirect ophthalmoscope in which the observation-light-beam deflecting mirrors are movable independently from the oculars and which therefore allows the operator to observe an eye irrespectively of pupil diameter or direction of observation.

To achieve the above objects, the binocular indirect ophthalmoscope according to the present invention has: a first reflecting surface for directing illuminating light to an eye under test; second and third reflecting surfaces for splitting and reflecting the reflected light from the eye under test to the left and to the right respectively; and fourth and fifth reflecting surfaces for directing the reflected light from said second and third reflecting surfaces to a left ocular and to a right ocular respectively, said binocular indirect ophthalmoscope being characterized by:

first and second actuating shafts extending laterally, or to the right-and to the left, and parallel to a plane containing the optical axes of said left and right oculars, the first actuating shaft being provided with: a first actuating handle for rotating the first actuating shaft; first converter means for converting the rotation of the first actuating shaft into a rectilinear movement of the first reflecting surface in a direction perpendicular to the plane; and a second actuating handle which is rotatable with said first actuating handle;

the second actuating shaft being interlocked with the second actuating handle such that they are rotatable together, the second actuating shaft being provided with second and third converter means which are laterally slidable on, and rotatable with, the second actuating shaft;

the second and third converter means being connected to the fourth and fifth reflecting surfaces, respectively, such that the fourth and fifth reflecting surfaces are moved toward or away from each other as the second and third converter means rotate together with said second actuating shaft; and the lateral sliding movement of the second converter means being accompanied by the lateral movement of the left ocular, the lateral sliding movement of the third converter means being accompanied by the lateral movement of the right ocular.

If the operator actuates the first actuating handle to thereby rotate the first actuating shift of the binocular indirect ophthalmoscope according to the present invention, rotation of the first actuating shaft is converted by first converter means into a rectilinear upward or downward movement of the first reflecting surface in a direction perpendicular to the plane containing the optical axes of the left and right oculars. Such rectilinear movement of the first reflector surface will raise or lower the position or passage of the illuminating light beam projected from the first reflector surface to the eye fundus under test.

Meanwhile, if the operator rotates the second actuating shaft by actuating the second actuating handle, the second and third converter means will rotate together with the second actuating shaft and thus the fourth and fifth reflecting surfaces are moved toward or away from each other by the second and third converter means.

Moreover, if the operator actuates the first and second actuating handles simultaneously, the above-described movement of the first, fourth and fifth reflecting surfaces will occur simultaneously.

Further, if the operator moves the left ocular laterally, the fourth reflecting surface is moved laterally together with the left ocular by the second converter means. Likewise, if the operator moves the right ocular laterally, the fifth reflecting surface is moved laterally together with the right ocular by the third converter means.

BRIEF DESCRIPTION OF THE DRAWINGS

The present invention will now be described, by way of example, with reference to the accompanying drawings, in which:

FIG. 7 is a diagram showing the optical configuration of a prior art binocular indirect ophthalmoscope; and FIGS. 8A, 8B and 8C are diagrams showing the relationship between a pupil, effective observation light beams and an effective illuminating light beam.

DESCRIPTION OF A PREFERRED EMBODIMENT

Figure 5:
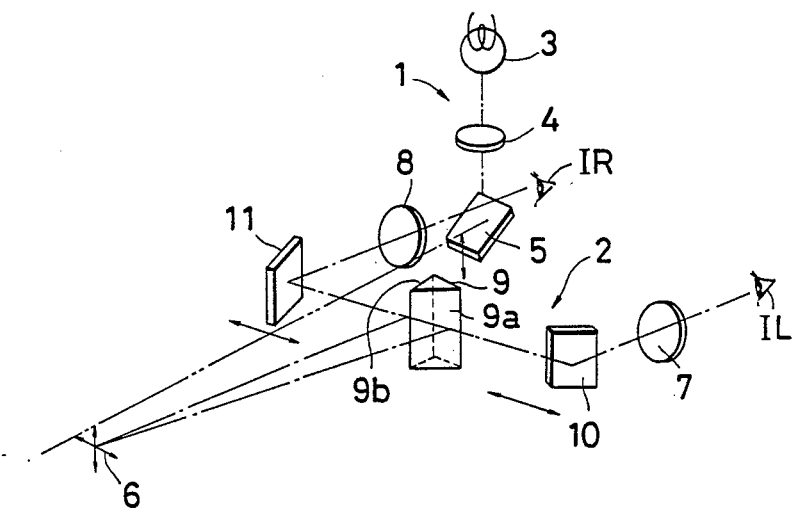
FIGS. 5 and 6 are illustrations showing the optical system of the binocular indirect ophthalmoscope shown in FIGS. 1 and 2.

FIG. 5 shows the optical system of an embodiment of the binocular indirect ophthalmoscope according to the present invention, in which an asperical lens (not shown) is placed between the scope and an eye under test(not shown).

The binocular indirect ophthalmoscope has an illuminating optical system 1 and an observation optical system 2.

The illuminating optical system 1 is arranged such that an illuminating light beam from an illuminating light source 3 is guided through a projection lens 4 and via a first reflecting mirror 5, or first reflecting surface, toward the aspherical lens. The illuminating light beam is projected through the aspherical lens onto the eye fundus under test, and it is reflected therefrom.

The reflected light beam from the eye fundus under test is guided through the aspherical lens to the observation optical system 2 of the binocular indirect ophthalmoscope. The aspherical lens forms, depending on the reflected light beam, an aerial image 6 of the eye fundus under test between itself and the observation optical system 2.

Figure 6:
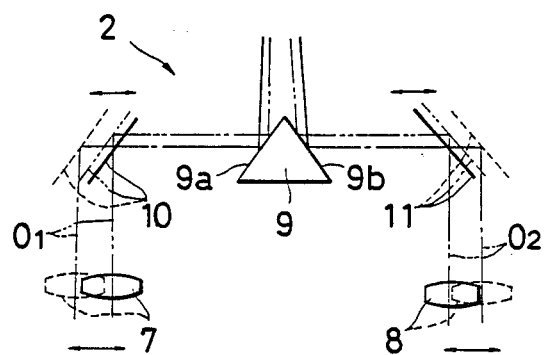

As shown in FIGS. 5 and 6, the observation optical system 2 has a left ocular 7, a right ocular 8, a center reflecting member 9 provided with second and third reflecting mirrors or reflecting surfaces 9a, 9b, and fourth and fifth reflecting mirrors or reflecting surfaces 10, 11 for reflecting the reflected light beams from the second and third reflecting mirrors 9a, 9b toward the left and right oculars 7, 8, respectively.

Figure 1:
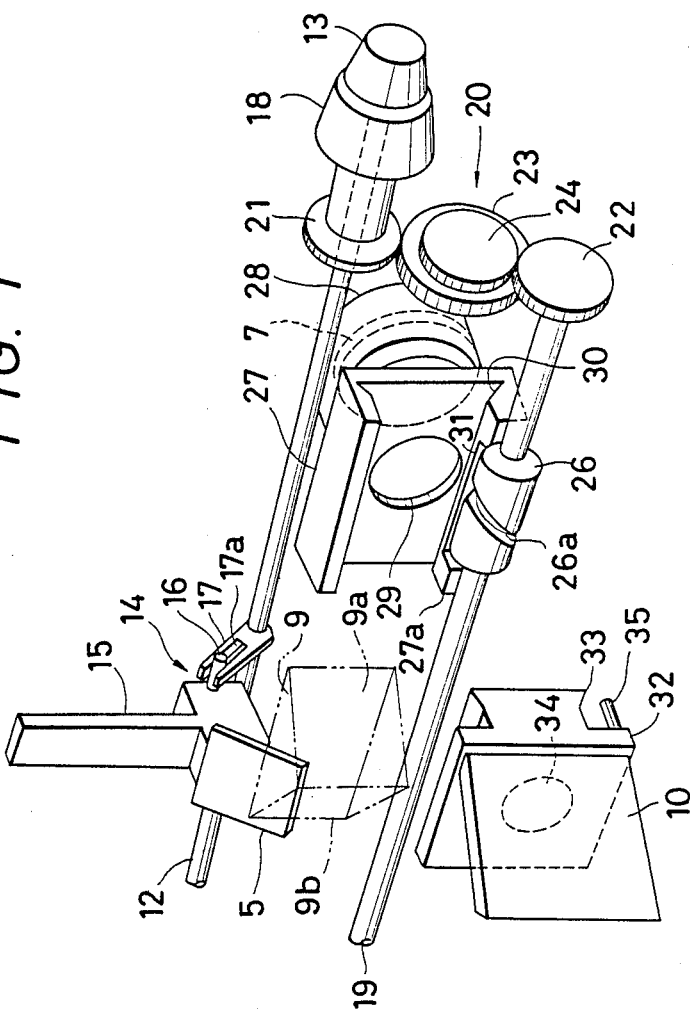
FIGS. 1 and 2 are perspective views showing principal parts of an embodiment of the binocular indirect ophthalmoscope according to the present invention.
Figure 2:
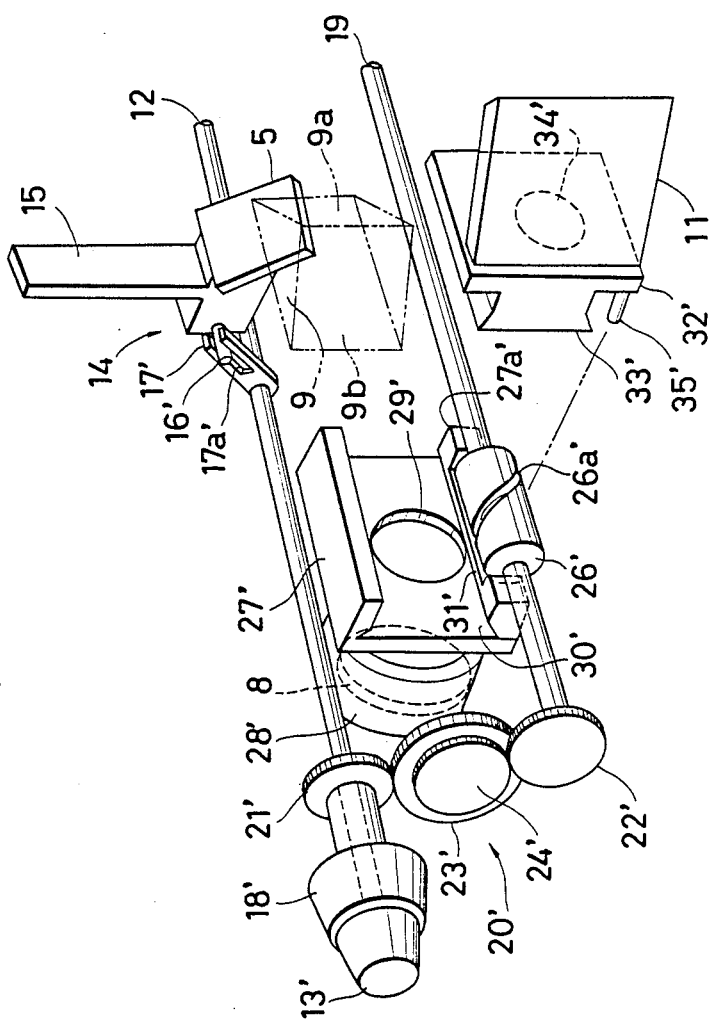

As shown in FIGS. 1 and 2, a first actuating shaft 12 is provided behind the first reflecting mirror 5 and extends laterally and parallel to the plane in which the optical axes 01, 02 of the left and right oculars 7, 8 lie. The first actuating shaft 12 is rotatably supported on a housing (not shown) and has first actuating handles 13, 13' secured to the ends thereof projecting out of the housing (not shown).

Between the first actuating shaft 12 and the first reflecting mirror 5, there is provided first converter means 14 for converting the rotation of the first actuating shaft 12 into a rectilinear motion of the first reflecting mirror 5 in a direction perpendiclular to the plane containing the optical axes 01, 02, whereby the mirror 5 can move vertically toward and away from the plane.

The converter means 14 includes a guide plate 15 vertically movably mounted on the housing (not shown), engaging pins 16, 16' projecting from opposite sides of the lower end of the guide plate 15 and U-shaped drive links 17, 17' which are, with one ends thereof, connected with the actuating shaft 12 and located on opposite sides of the guide plate 15. The drive links 17, 17' have slits 17a, 17a' formed in their free ends. An engaging pin 16, 16' is inserted into each of the slits 17a, 17a'.

The second actuating handle 18, 18' is rotatably mounted on the first actuating shaft 12 adjacent to each end thereof. The second actuating handles 18, 18' are located next to the first actuating handles 13, 13' respectively, and the pairs of neighboring first and second handles 13 and 18 or 13' and 18' can be rotated together. Further, a second actuating shaft 19 is provided below and forwardly of and parallel to the first actuating shaft 12. The second shaft 19 also is rotatably mounted on the housing (not shown). The second actuating handles 18, 18' are interlocked with the second actuating shaft 19 by means of rotary transmission means 20, 20'.

The rotary transmission means 20 comprises a first gear 21 connected with the second actuating handle 18, a second gear 22 secured to one end of the second actuating shaft 19, a third gear 23 rotatably mounted on the housing (not shown) and engaging with the first gear 21, and a fourth gear 24 provided integrated with the third gear 23 and engaging with the second gear 22. The other rotary transmission means 20' has a similar construction, identical parts being designated by identical but primed reference numerals, so that a detailed description thereof will not be given.

Figure 3:
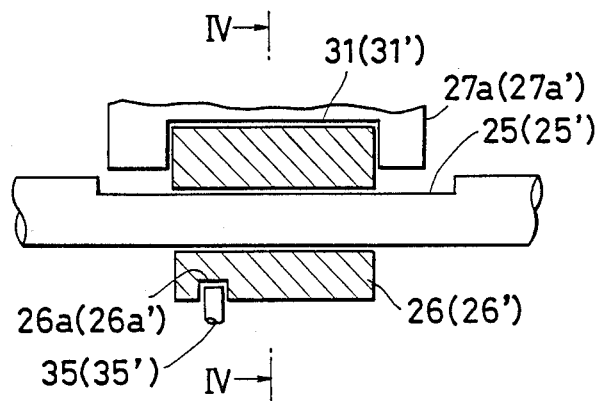
FIG. 3 is a sectional vie showing a cam barrel along a second actuating shaft shown in FIGS. 1 and 2.
Figure 4:
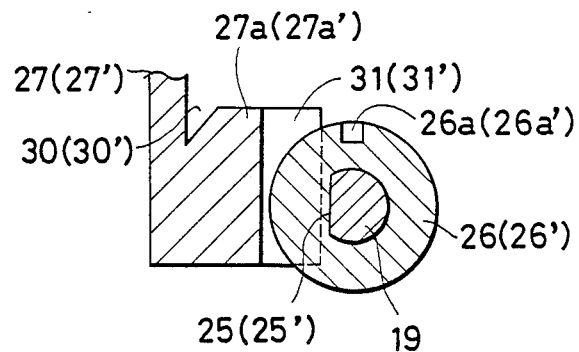
FIG. 4 is a sectional view taken along lines IV—IV shown in FIG. 3.

The second actuating shaft 12 has axially extending guide planes 25, 25' formed thereon adjacent to each end thereof, as shown in FIGS. 3 and 4. Second and third converter means in the form of cam barrels 26, 26' respectively, are axially movably fitted on the second actuating shaft 12 at the portions thereof formed with the guide planes 25, 25'. The cam barrels 26, 26' are allowed to move axially but are prohibited from rotation relative to the second actuating shaft 12. One cam barrel 26 has a left-hand helical cam groove 26a formed on the periphery thereof, while the other cam barrel 26' has a right-hand helical cam groove 26a' formed on the periphery thereof.

Rearwardly of the cam barrels 26, 26', ocular mounts in the form of left and right mounts 27, 27', respectively, are provided. The left side mount 27 has a left side lens barrel 28 integrated therewith, while the right side mount 27' has a right side lens barrel 28' integrated therewith. Further, the left and right mounts 27, 27' are formed with openings 29, 29', respectively, which are coaxial with and communicated to the left and right lens barrels 27, 27', respectively. The left and right lens barrels 27, 27' have the above-mentioned left and right oculars 7, 8, respectively, mounted therein. Further, the mounts 27, 27' are provided with dovetail grooves 30, 30', respectively, which are open forwardly and extend laterally. The mounts 27, 27' have lower flanges 27a, 27a' which in turn have depressions 31, 31'. The cam barrels 26, 26' are engaged in these depressions 31, 31' and are rotatable but laterally immovable relative to them. The left and right mounts 27, 27' so constructed are laterally movably mounted on guide segments of the housing (not shown).

Dovetails 33, 33' of left and right mirror mounts 32, 32' are laterally movably fitted in the dovetail grooves 30, 30' of the left and right ocular mounts 27, 27'. The left and right mirror mounts 32, 32' have the fourth and fifth reflecting mirrors 10, 11, respectively, securedly mounted on the front sides thereof. The mirror mounts 32, 32' have openings 34, 34' therethrough, respectively, which correspond to the fourth and fifth reflecting mirrors 10, 11 and which lead to the openings 29, 29'. In addition, the left and right mirror mounts 32, 32' have guide pins 35, 35' integrated therewith which are engaged with the helical cam grooves 26a, 26a' of the cam barrels 26, 26'. The helical cam grooves 26a, 26a' and cooperating guide pins 35, 35', when actuated by rotating the second actuating shaft 12, will move the fourth and fifth reflecting mirrors or reflecting surfaces 10, 11 toward or away from each other. Further, the combination of the helical cam groove 26a and guide pin 35 will move the fourth reflecting mirror or reflecting surface 10 laterally together with the cam barrel or second converter means 26 when the left mirror mount 32 is moved laterally. Similarly, the combination of the other helical groove 26a' and guide pin 35' will move the fifth reflecting mirror or reflecting surface 11 laterally together with the other cam barrel or third converter means 26' when the right mirror mount 32' is moved laterally.

Next, a description will be given of the operation of the so constructed binocular indirect ophthalmoscope.

First, if the operator rotates the first handle 13 or 13' to rotate the first actuating shaft 12, the drive links 17, 17' will rotate with the first shaft 12, whereby the engaging pins 16, 16' are displaced upwardly or downwardly. The guide plate 15 is thereby displaced rectilinearly upwardly or downwardly and the first reflecting mirror or reflecting surface 5 is moved together upwardly or downwardly. The rotation of the first actuating shaft 12 is thus be converted by the first converter means 14 into an upward or downward rectilinear movement which will cause the first reflecting mirror 5 to move toward or away from, or downwardly or upwardly, the plane which contains the optical axes 01, 02 of the left and right oculars 7, 8. Thus, the passage of the illuminating beam projected via the first reflecting mirror 5 to the eye fundus under test can be shifted upwardly or downwardly. Thus, the distance H between the effective illuminating light beam IF and the effective observation light beams OFL, OFR shown in FIG. 8 can be changed.

On the other hand, rotation of the second actuating handle 18 or 18' is transmitted through a train of gear 21-24 or 21'-24' to the second actuating shaft 19. The cam barrels 26, 26', or the second and third converter means, mounted on the second actuating shaft 19 will rotate together with this shaft 19. The guide pins 35, 35' engaged in the helical cam grooves 26a, 26a' of the cam barrels 26, 26' are moved laterally toward or away from each other by the thus rotating cam barrels, whereby the left and right mirror mounts 32, 32' are moved laterally relative to the left and right ocular mounts 27, 27'. Consequently, the fourth and fifth reflecting surfaces, or fourth and fifth reflecting mirrors 10, 11, integrated with the mirror mounts 32, 32' are moved laterally toward or away from each other. This will change the distance D between the effective illuminating light beams OFL, OFR, from the eye fundus under test as observed by the left and right eyes IL. IR.

If the operator actuates the first and second handles 12, 18 or 12', 18' simultaneously, the first, fourth and fifth reflecting mirrors 5, 10, 11 are moved simultaneously in the above-described manner. This brings about simultaneous changes in the above-described distances H, D. In this regard, simultaneous rotation of the first and second handles 12, 18 or 12', 18' through the same angle will bring about an amount of vertical movement of the first reflecting mirror 5 and the same amount of simultaneous lateral movement of the fourth and fifth reflecting mirrors 10, 11, so that the distances D, H shown in FIG. 8A can be easily adjusted into distances d, h shown in FIG. 8C.

Further, if the operator moves the left lens barrel 28 containing the left ocular 7 laterally, the left mount 27 integrated with the left lens barrel 28 will move laterally and the cam barrel 26 as the second converter means will also move laterally together with the left mount 27 and left lens barrel 28. Since the cam barrel 26 will not rotate during such lateral movement, the left mirror mount 32 also will be moved laterally together with the left lens barrel 28 by means of the helical cam groove 26a moves the right lens barrel 28' containing the right ocular 8 laterally, the right mount 27' integrated with the right lens barrel 28' will move laterally and the cam barrel 26' as the third converter means will also move laterally together with the right mount 27' and right lens barrel 28'. Since the cam barrel 26' will not rotate during such lateral movement, right mirror mount 32' also will be moved laterally together with the right lens barrel 28' by means of the helical cam groove 26a' and the engaging guide pin 35'. Since the left and right lens barrels 28, 28' can thus be moved laterally, the optical axes of the left and right oculars 7, 8 can be easily and rapidly adjusted for different operators having different eye-to-eye distances.

In the binocular indirect ophthalmoscope according to the present invention, the height at which the effective illuminating light beam lies can be changed by means of the first actuating handle and the first converter means, and moreover the distance between the effective observation light beams OFL, OFR. i.e. the base length of the stereoscope, can also be changed by means of the second actuating handle and the second and third converter means. Thus, regardless of the observation direction or of the pupil diameter of the eye under test, the effective illuminating light beam can be shifted such that it is not eclipsed by the iris, whereby better illumination and better stereoscopic observation can be achieved.

In addition, since the first and second actuating handles are placed adjacent to each other, it is possible to simultaneously actuate these first and second handles thereby to simultaneously adjust the height of the effective illuminating light beam and the distance, or base length, between the effective observation light beams OFL. OFR.

Further, in the apparatus according to the invention, the left and right oculars are laterally movable together with said second and third converter means respectively, and are rotatable relative to said second and third converter means; said fourth reflecting surface is connected to said second converter means such that they ar laterally movable together; said fifth reflecting surface is connected to said third converter means such that they are laterally movable together. Therefore, the apparatus allows the operator to easily and rapidly adjust the distance between the left and right ocular optical axes for him.

What is claimed is:

1. A binocular indirect ophthalmoscope having: a first reflecting surface for directing illuminating light to an eye under test; second and third reflecting surfaces for splitting and reflecting the reflected light from the eye under test to the left and to the right respectively; and fourth and fifth reflecting surfaces for directing the reflected light from said second and third reflecting surfaces to a left ocular and to a right ocular respectively, said binocular indirect ophthalmoscope further comprising:

first and second actuating shafts extending laterally, or to the right and to the left, and parallel to a plane containing the optical axes of said left and right oculars, said first actuating shaft being provided with: a first actuating handle for rotating the first actuating shaft; first converter means for converting the rotation of said first actuating shaft into a rectilinear movement of said first reflecting surface in a direction perpendicular to said plane; and a second actuating handle which is rotatable with said first actuating handle;

said second actuating shaft being interlocked with the second actuating handle such that they are rotatable together, the second actuating shaft being provided with second and third converter means which are laterally slidable on, and rotatable with, the second actuating shaft;

the second and third converter means being connected to said fourth and fifth reflecting surfaces, respectively, such that said fourth and fifth reflecting surfaces are moved toward or away from each other as the second and third converter means rotate together with said second actuating shaft; and the lateral movement of said second converter means being accompanied by the lateral movement of said left ocular, and the lateral movement of said third converter means being accompanied by the lateral movement of said right ocular.

2. The binocular indirect ophthalmoscope as claimed in claim 1, in which said second and third converter means comprise: left and right cam barrels provided adjacent to both ends of the second actuating shaft and having helical cam grooves extending in the opposite directions; and left and right mirror mounts each engaging with corresponding one of said helical grooves and each having either said fourth or fifth reflecting surface, in which each of said left and right cam barrels is mounted on the second actuating shaft such that it is slidable in the direction of extension of the second actuating shaft and rotatable with the second actuating shaft, and in which each of the left and right cam barrels is engaged with one of said left and right ocular mounts such that they are movable together in the direction of extension of said second actuating shaft.

3. The binocular indirect ophthalmoscope as claimed in claim 1, in which said second and third converter means comprise: engaging pins formed on each of said left and right mirror mounts having said fourth and fifth reflecting surfaces; and cam groove formed in said second shaft and holding the engaging pins therein for moving said left and right mirror mounts toward or away from each other in the direction of extension of the second actuating shaft, in which each of said left and right mirror mounts has one of said left and right ocular mounts mounted thereon such that the latter is slidable in the direction of extension of said second actuating shaft, whereby the distance between the optical axes of said left and right ocular mounts can be adjusted.

4. The binocular indirect ophthalmoscope as claimed in claim 1, in which said left and right ocular mounts are respectively connected to said left and right mirror mounts by means of dovetail grooves extending in the direction of extension of said second actuating shaft and dovetails slidably fitted in said dovetail grooves, in which said second and third converter means respectively comprise left and right cam barrels slidably fitted in said second shaft and engaged with said engaging pins of said left and right mirror mounts for moving said mirror mounts toward and away from each other, and in which each of said left and right ocular mounts is engaged with corresponding one of the cam barrels in such a manner that it allows the latter to rotate and it can move with the latter.

5. The binocular indirect ophthalmoscope as claimed in any of claims 1 through 4, in which said first converter means includes: a guide plate which is movable upwardly and downwardly in a direction perpendicular to the plane containing the optical axes of said left and right oculars; engaging pins formed on and projecting from both left and right sides of said guide plate; and U-shaped drive links provided on said first actuating shaft and engaged with said engaging pins.

6. The binocular indirect ophthalmoscope as claimed in any of claims 1 through 4, in which rotary transmission means comprising gear mechanisms is provided between said second actuating handle and said second actuating shaft.

7. The binocular indirect ophthalmoscope as claimed in any of claims 1 through 4, in which said first and second actuating handles are mounted on the ends of said first actuating shaft and arranged adjacent to each other such that they can rotate together.

* * * * *